United States Patent
Moscrip et al.

(10) Patent No.: US 6,868,738 B2
(45) Date of Patent: *Mar. 22, 2005

(54) METHOD AND APPARATUS FOR DETERMINING THE ANGLE OF GYRATION AND/OR THE PRESSURE IN A GYRATORY COMPACTOR

(75) Inventors: William Matthew Moscrip, Durham, NC (US); William A. Gowan, Raleigh, NC (US)

(73) Assignee: Troxler Electronic Laboratories, Inc., Research Triangle Park, NC (US)

( * ) Notice: Subject to any disclaimer, the term of this patent is extended or adjusted under 35 U.S.C. 154(b) by 197 days.

This patent is subject to a terminal disclaimer.

(21) Appl. No.: 10/210,020

(22) Filed: Jul. 31, 2002

(65) Prior Publication Data

US 2004/0020306 A1 Feb. 5, 2004

(51) Int. Cl.[7] ............................................. G01N 3/00
(52) U.S. Cl. ....................................................... 73/818
(58) Field of Search ......................... 73/818, 821, 824, 73/825

(56) References Cited

U.S. PATENT DOCUMENTS

| | | | |
|---|---|---|---|
| 4,087,918 A | | 5/1978 | Schmid et al. |
| 5,275,056 A | * | 1/1994 | Hamilton et al. ............. 73/794 |
| 5,323,655 A | | 6/1994 | Eagan et al. |
| 5,365,793 A | * | 11/1994 | Terrel et al. .................. 73/813 |
| 5,456,118 A | | 10/1995 | Hines et al. |
| 5,606,133 A | | 2/1997 | Hines et al. |
| 5,817,946 A | | 10/1998 | Brovold |
| 5,824,913 A | * | 10/1998 | Pyle ............................. 73/818 |
| 5,939,642 A | | 8/1999 | King et al. |
| 6,026,692 A | | 2/2000 | Brovold |
| 6,477,783 B1 | * | 11/2002 | Harman et al. ............... 33/534 |
| 6,526,836 B1 | * | 3/2003 | Brouse ........................ 73/818 |
| 6,595,068 B2 | * | 7/2003 | Brovold et al. ............... 73/803 |
| 2001/0049969 A1 | | 12/2001 | Bahia et al. |
| 2003/0075820 A1 | | 4/2003 | Hines |

OTHER PUBLICATIONS

Test Quip, Inc.: Internet Article, Online. XP-002265535. Retrieved from the Internet: URL:http:///www.testquip.com/avk.html, retrieved on Dec. 17, 2003.

* cited by examiner

*Primary Examiner*—Max Noori
(74) *Attorney, Agent, or Firm*—Alston & Bird LLP

(57) ABSTRACT

An apparatus adapted to interact with a cylindrical mold for a gyratory compactor so as to determine a property of the gyratory compactor is provided, wherein the mold is adapted to contain a sample therein. Such an apparatus comprises a rigid disk-shaped plate defining an axis and a periphery, with the plate being adapted to be disposed within the mold. At least one sensing device is operably engaged with the plate, wherein the at least one sensing device is configured to measure a proximity of the at least one sensing device with respect to a reference member and to produce a corresponding signal indicative of the property of the gyratory compactor. In one embodiment, the apparatus is configured to determine the gyration angle of the mold, while in another embodiment, the apparatus is configured to determine the pressure exerted on the sample within the mold. The property of the mold may be determined either statically or dynamically. Associated apparatuses, devices, systems, and methods are also provided.

38 Claims, 10 Drawing Sheets

US 6,868,738 B2

METHOD AND APPARATUS FOR DETERMINING THE ANGLE OF GYRATION AND/OR THE PRESSURE IN A GYRATORY COMPACTOR

BACKGROUND OF THE INVENTION

1. Field of the Invention

The present invention relates to a device for measuring a property of a gyratory compactor device and, more particularly, to a method and apparatus for determining an angle of gyration and/or a pressure in a Superpave gyratory compactor.

2. Description of Related Art

The Strategic Highway Research Program (SHRP) has developed a standard for testing the physical properties of a bituminous asphalt paving mix, using a device known as the Superpave gyratory compactor. The Superpave gyratory compactor produces compacted cylindrical test samples of the asphalt paving mix for determining volumetric and mechanical properties. The compactor simulates the kneading action of the large rollers used to compact asphalt pavement during highway construction. Thus, the compacted samples simulate the density, aggregate orientation, and structural characteristics obtained in an actual roadway when proper construction procedures are used in the placement of the paving mix. Typically, a sample of the asphalt paving mix is placed in an open-ended cylindrical mold, with circular disks or plugs being placed at opposite ends of the mold. The gyratory compactor device applies pressure through these disks to the sample in the mold while gyrating the mold at a specified angle to produce a gyratory kneading action. The Superpave gyratory compactor specifications call for the mold to be gyrated at a compaction angle of 1.25 degrees, operating at 30 rpm, while applying a constant pressure of 600 kPa.

Several manufacturers produce gyratory compactors according to the Superpave gyratory compactor specifications. Gyratory compactors of this type are described for example in the following U.S. Pat. Nos. 5,323,655; 5,456,118; 5,606,133; 5,939,642; 5,817,946; and 6,026,692.

During the compaction process, the gyratory compactor machine records the number of gyratory revolutions, the height of the test sample (or more accurately, the position or movement of the pressure ram) and other parameters. In order to have consistent and reproducible results from one machine to another, each machine must be calibrated. These calibrations include measurement of the mold angle (otherwise referred to herein as the "angle of gyration" or "gyration angle") and measurement of the pressure applied by the pressure ram. Heretofore, the mold angle calibration has been typically carried out in a static mode, wherein the mold angle is mechanically set and calibrated during the initial assembly phase and not adjusted thereafter unless required. The particular method of adjustment generally differs between different machine designs, but usually involves a complex arrangement of sliding surfaces in the form of, for example, cams, pins and slots, linkages, and/or the like. The mold angle adjustment mechanism thus serves to provide an offset between one end of the mold, held in alignment with the ram axis, and the other end of the mold, which is compelled to move in a circular orbit by the kinematic properties of the machine. However, a calibration carried out in a static mode will not necessarily take into account whether the configuration of the gyratory compactor maintains the mold angle within specifications throughout the entire compaction process. Therefore, the angle of gyration must be occasionally verified. However, the correct angle typically can only be verified by a complete re-calibration of the machine and such a re-calibration is often not practical in the field. As such, re-calibration usually requires that the machine be shipped back to the manufacturer, or requires the presence of a factory technician at the site, each of which may involve a sizeable expenditure of time and money.

In other instances, mechanical-type contact sensors have been employed to determine the mold angle. For example, U.S. Pat. No. 5,817,946 to Brovold describes multiple mold angle transducers, each comprising a spring-biased plunger, wherein the tip of the plunger continuously contacts and rests against the outer surface of the cylinder wall of the mold. The relative displacements of the plungers thereby enable the determination of the mold angle. However, the compaction process is a dynamic process, with the mold being constantly gyrated while pressure is applied. Accordingly, the plungers may be prone to wear or misalignment from contact with the mold during the compaction process, thereby making it difficult to maintain calibration and receive consistent measurements from the transducers. Further, such mechanical displacement-measuring devices may not provide the necessary accuracy for measuring the mold angle in accordance with the SHRP standard. In some instances, accretions on the wall of the mold from sample processing may further decrease the accuracy of the mechanical-type contact sensors. These and other factors can affect the actual mold angle measured and indicated during the compaction process.

In addition, the pressure calibration of the machine has also been typically carried out only in a static mode. For example, a load cell can be temporarily positioned in contact with the pressure ram of the compactor to measure the force applied by the ram. However, a calibration carried out in a static mode will not take into account whether the control system of the gyratory compactor holds the pressure within specifications throughout the entire compaction process. The compaction process is a dynamic process, with the mold being constantly gyrated while pressure is applied. Also, the sample within the mold is reduced in height as it is compacted. These and other factors can affect the actual pressure applied to the sample by the gyratory compactor.

Thus, there exists a need for an apparatus, system, and method capable of statically and dynamically determining and indicating the angle of gyration of a mold as well as the pressure exerted on a sample contained therein so as to provide a consistent and readily calibrated mechanism for verifying compliance with the SHRP standard for testing the physical properties of a bituminous asphalt paving mix using a Superpave gyratory compactor, as well as other improvements over existing devices.

BRIEF SUMMARY OF THE INVENTION

The above and other needs are met by the present invention which, in one embodiment, provides an apparatus adapted to interact with a cylindrical mold for a gyratory compactor so as to determine a property of the gyratory compactor, wherein the mold is adapted to contain a sample therein. Such an apparatus includes a rigid disk-shaped plate defining an axis and a periphery, the plate being further adapted to be disposed within the mold. At least one sensing device is operably engaged with the plate, wherein the at least one sensing device is configured to measure a proximity of the reference member with respect to the at least one proximity-sensing device and to produce a corresponding signal indicative of the property of the gyratory compactor. In one embodiment, the apparatus is configured to determine the gyration angle of the mold, while in another embodiment, the apparatus is configured to determine the pressure exerted on the sample within the mold.

Another advantageous aspect of the present invention comprises an apparatus adapted to interact with a cylindrical mold for a gyratory compactor so as to determine a gyration angle of the mold, wherein the mold is adapted to contain a sample therein. Such an apparatus includes a rigid disk-shaped plate defining an axis and a periphery. The plate is adapted to be disposed within the wall of the cylindrical mold in communication with the sample. At least one sensing device is operably engaged with the plate so as to be spaced apart from and cooperable with the wall when the plate is disposed within the mold. The at least one sensing device is configured to produce a signal corresponding to the angle of the wall with respect to the axis of the plate such that the signal is thereby indicative of the gyration angle of the mold.

Still another advantageous aspect of the present invention comprises an apparatus adapted to interact with a gyratory compactor so as to determine a gyration angle. Such an apparatus includes an open-ended cylindrical mold having a wall defining an inner diameter, wherein the mold is adapted to contain a sample therein for compaction by the gyratory compactor. A rigid disk-shaped plate defining an axis and a periphery and having a diameter corresponding substantially to the inner diameter of the mold is adapted to be disposed within the mold in communication with the sample. At least one sensing device is operably engaged with the plate so as to be spaced apart from and cooperable with the wall when the plate is disposed within the mold. The at least one sensing device is configured to produce a signal corresponding to the angle of the wall with respect to the axis of the plate such that the signal is thereby indicative of the gyration angle of the mold.

Yet another advantageous aspect of the present invention comprises a system for determining a gyration angle in a gyratory compactor. Such a system includes a gyratory compactor apparatus and an open-ended cylindrical mold having a wall defining an inner diameter, wherein the mold is configured to be operably engageable with the gyratory compactor apparatus and is adapted to contain a sample therein for compaction by the gyratory compactor. A rigid disk-shaped plate defining an axis and a periphery and having a diameter corresponding substantially to the inner diameter of the mold is adapted to be disposed within the mold in communication with the sample. At least one sensing device is operably engaged with the plate so as to be spaced apart from and cooperable with the wall when the plate is disposed within the mold. The at least one sensing device is configured to produce a signal corresponding to the angle of the wall with respect to the axis of the plate such that the signal is thereby indicative of the gyration angle of the mold.

Still another advantageous aspect of the present invention comprises a method of determining a gyration angle of an open-ended cylindrical mold for a gyratory compactor, wherein the mold is adapted to contain a sample therein. First, at least one sensing device is inserted into an open end of the mold having a wall defining an inner diameter. The at least one sensing device is operably engaged with a rigid disk-shaped plate defining an axis and having a diameter corresponding substantially to the inner diameter of the mold, wherein the at least one sensing device is disposed about a periphery of the plate so as to be spaced apart from and cooperable with the wall when the plate is disposed within the mold. A signal is then received from the at least one sensing device. The signal corresponds to the angle of the wall with respect to the axis of the plate as dynamically determined by the at least one sensing device as the mold is being gyrated such that the signal is thereby indicative of the gyration angle of the mold.

Yet still another advantageous aspect of the present invention comprises a device adapted to dynamically measure a pressure exerted on a sample contained within a cylindrical mold of a gyratory compactor. Such a device includes a rigid disk-shaped plate defining an axis and a periphery and adapted to be disposed within the mold in communication with the sample. At least one proximity-sensing device is operably engaged with the plate, wherein the at least one proximity-sensing device is configured to dynamically measure the proximity of a reference member with respect to the at least one proximity-sensing device and to produce therefrom a signal corresponding to the pressure exerted on the sample within the mold.

Another advantageous aspect of the present invention comprises a system adapted to dynamically measure a pressure exerted on a sample contained within a cylindrical mold of a gyratory compactor. Such a system includes an open-ended cylindrical mold having an inner diameter and adapted to contain a sample therein for compaction by the gyratory compactor. A rigid disk-shaped plate, defining an axis and a periphery and having a diameter corresponding substantially to the inner diameter of the cylindrical mold, is adapted to be disposed within the mold in communication with the sample. At least one proximity-sensing device is operably engaged with the plate, wherein the at least one proximity-sensing device is configured to dynamically measure the proximity of a reference member with respect to the at least one proximity-sensing device and to produce therefrom a signal corresponding to the pressure exerted on the sample within the mold.

Still another advantageous aspect of the present invention comprises a system adapted to dynamically measure a pressure exerted on a sample contained within a cylindrical mold of a gyratory compactor. Such a system includes a gyratory compactor apparatus and an open-ended cylindrical mold having a wall defining an inner diameter, wherein the mold is configured to be operably engageable with the gyratory compactor apparatus and is adapted to contain a sample therein for compaction by the gyratory compactor. A rigid disk-shaped plate, defining an axis and a periphery and having a diameter corresponding substantially to the inner diameter of the mold, is adapted to be disposed within the mold in communication with the sample. At least one proximity-sensing device is operably engaged with the plate, wherein the at least one proximity-sensing device is configured to dynamically measure the proximity of a reference member with respect to the at least one proximity-sensing device and to produce therefrom a signal corresponding to the pressure exerted on the sample within the mold.

Yet another advantageous aspect of the present invention comprises a method of determining a pressure exerted on a sample contained within a cylindrical mold for a gyratory compactor. First, at least one proximity-sensing device is inserted into an open end of a mold having an inner diameter. The at least one proximity-sensing device is operably engaged with a rigid disk-shaped plate defining an axis and a periphery and having a diameter corresponding substantially to the inner diameter of the mold. The plate further comprises a disk-shaped base portion having a center and opposing faces and a ring-shaped portion coaxial with the center and extending from the periphery of one of the faces. The center of the base portion is configured to experience a deflection with respect to the periphery in response to pressure applied across the other face of the base portion. The at least one proximity-sensing device is mounted on a distal end of an arm having a proximal end mounted at the center and extending to the distal end substantially parallel to the base portion. A signal is then dynamically received from the at least one proximity-sensing device as the mold is being gyrated by the gyratory compactor. The signal corresponds to a proximity of a reference member with respect to the at least one proximity-sensing device, wherein the reference member is mounted on the base portion of the plate, away from the center and adjacent to the ring-shaped portion, so as to be adjacent to the at least one-proximity-sensing device. The deflection of the center in response to pressure results in a corresponding displacement of the arm and the at least one proximity-sensing device parallel to the axis. The reference member is configured with respect to the at least one proximity-sensing device such that the displacement of the arm parallel to the axis and away from the reference member is sensed by the at least one proximity-sensing device. The corresponding signal produced by the at least one proximity-sensing device is thereby indicative of the pressure exerted on the sample within the mold.

Thus, embodiments of the present invention provide apparatuses, devices, systems, and methods capable of statically and dynamically determining and indicating the angle of gyration of a mold as well as a pressure exerted on a sample contained therein so as to provide a consistent and readily calibrated mechanism for verifying compliance with the SHRP standard for testing the physical properties of a bituminous asphalt paving mix using a Superpave gyratory compactor. Accordingly, embodiments of the present invention provide significant advantages as further detailed herein.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

Figure 5A:
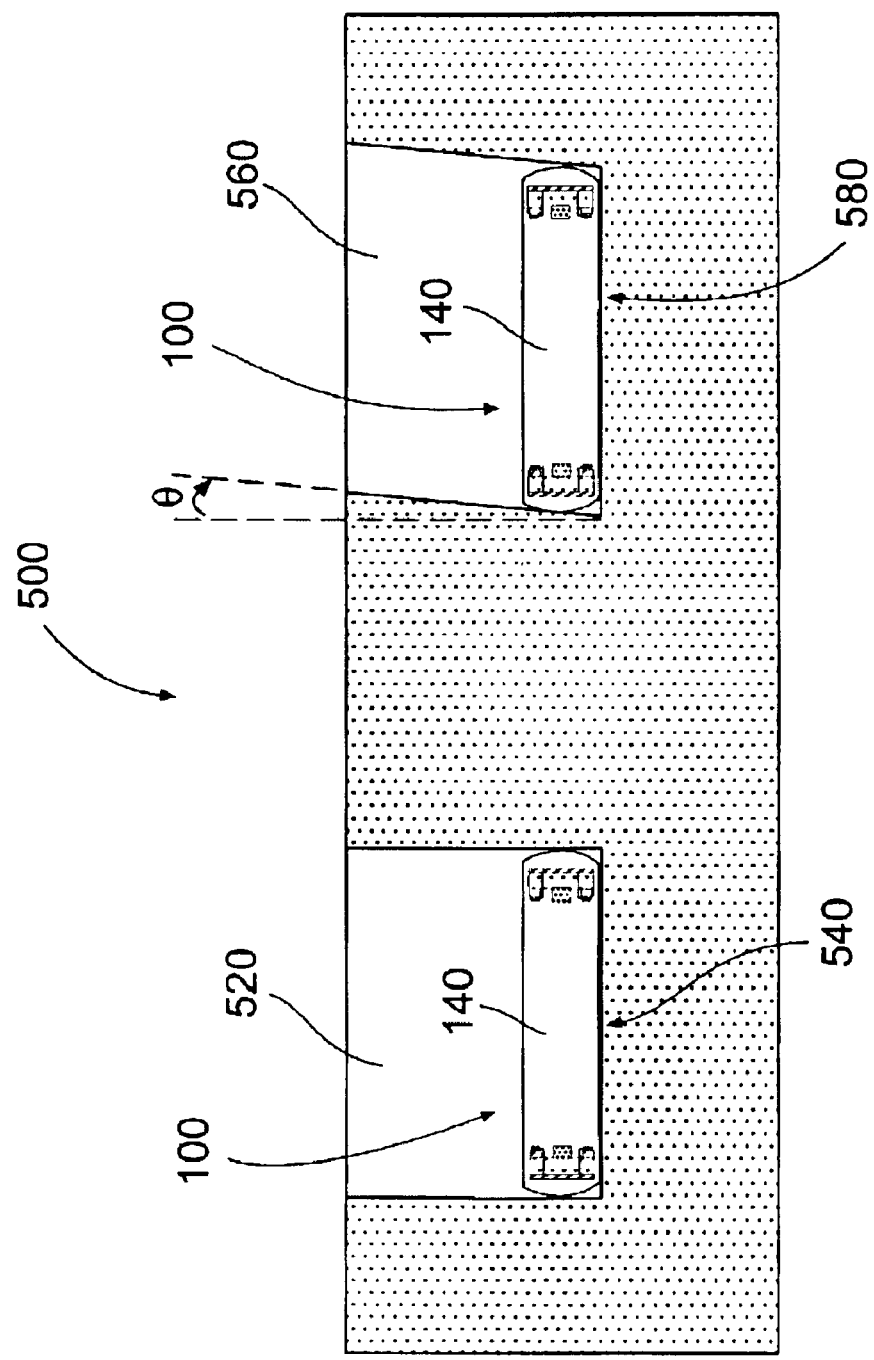
Figure 5B:
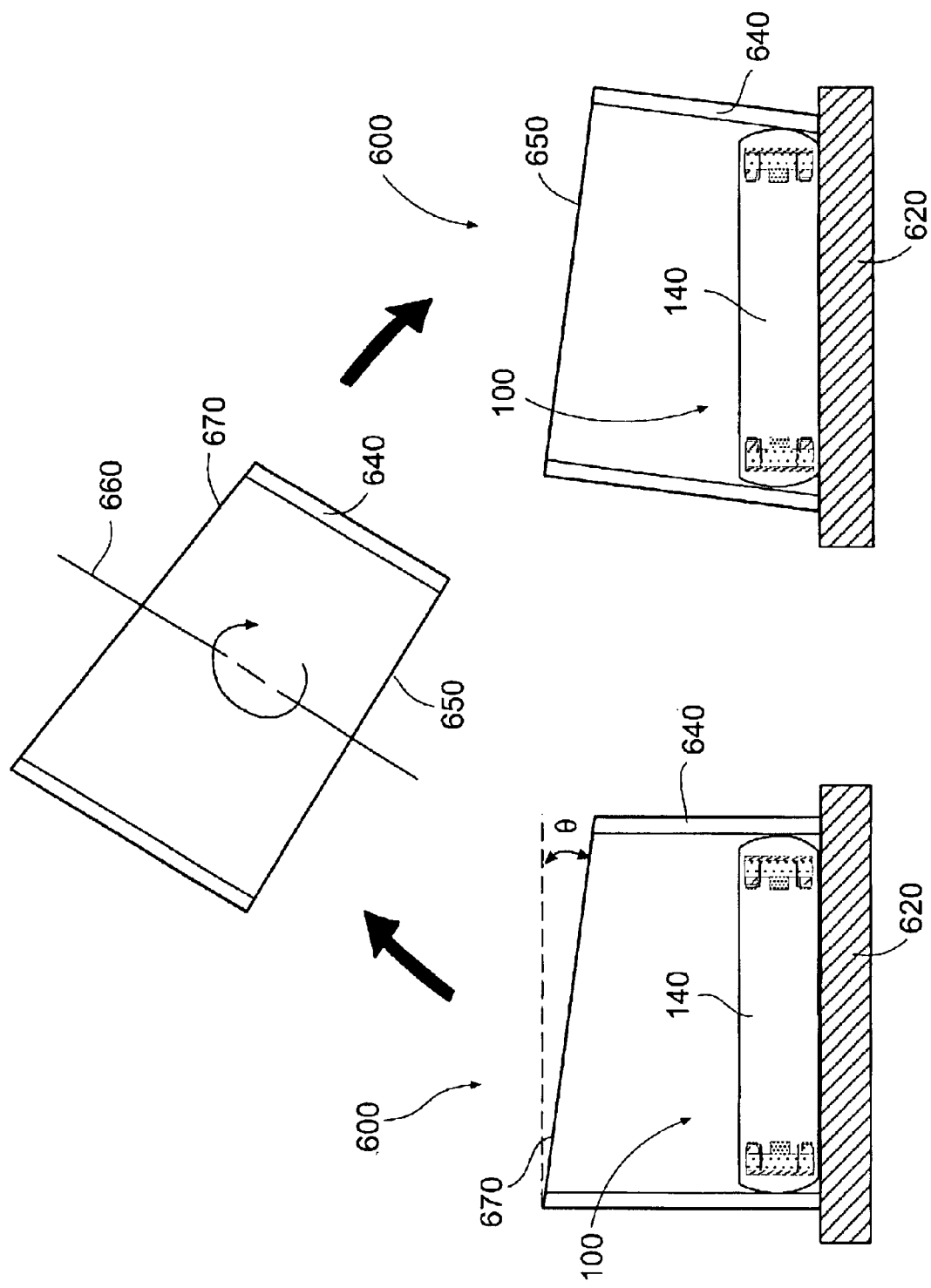

FIG. 5A is a cross-sectional schematic of a calibration device configured to allow calibration of an apparatus adapted to dynamically measure the gyratory angle of a mold for a gyratory compactor, according to one embodiment of the present invention; and FIG. 5B is a cross-sectional schematic of a calibration device configured to allow calibration of an apparatus adapted to dynamically measure the gyratory angle of a mold for a gyratory compactor, according to another embodiment of the present invention.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

A gyration angle measurement device according to the present invention is designed to be used with any of the Superpave gyratory compactors which are presently available commercially. Illustrative but non-limiting examples of gyratory compactors which can utilize such a gyration angle measurement device of the present invention are described in the following U.S. Pat. Nos. 5,323,655; 5,456,118; 5,606,133; 5,939,642; 5,817,946; and 6,026,692.

Figure 1:
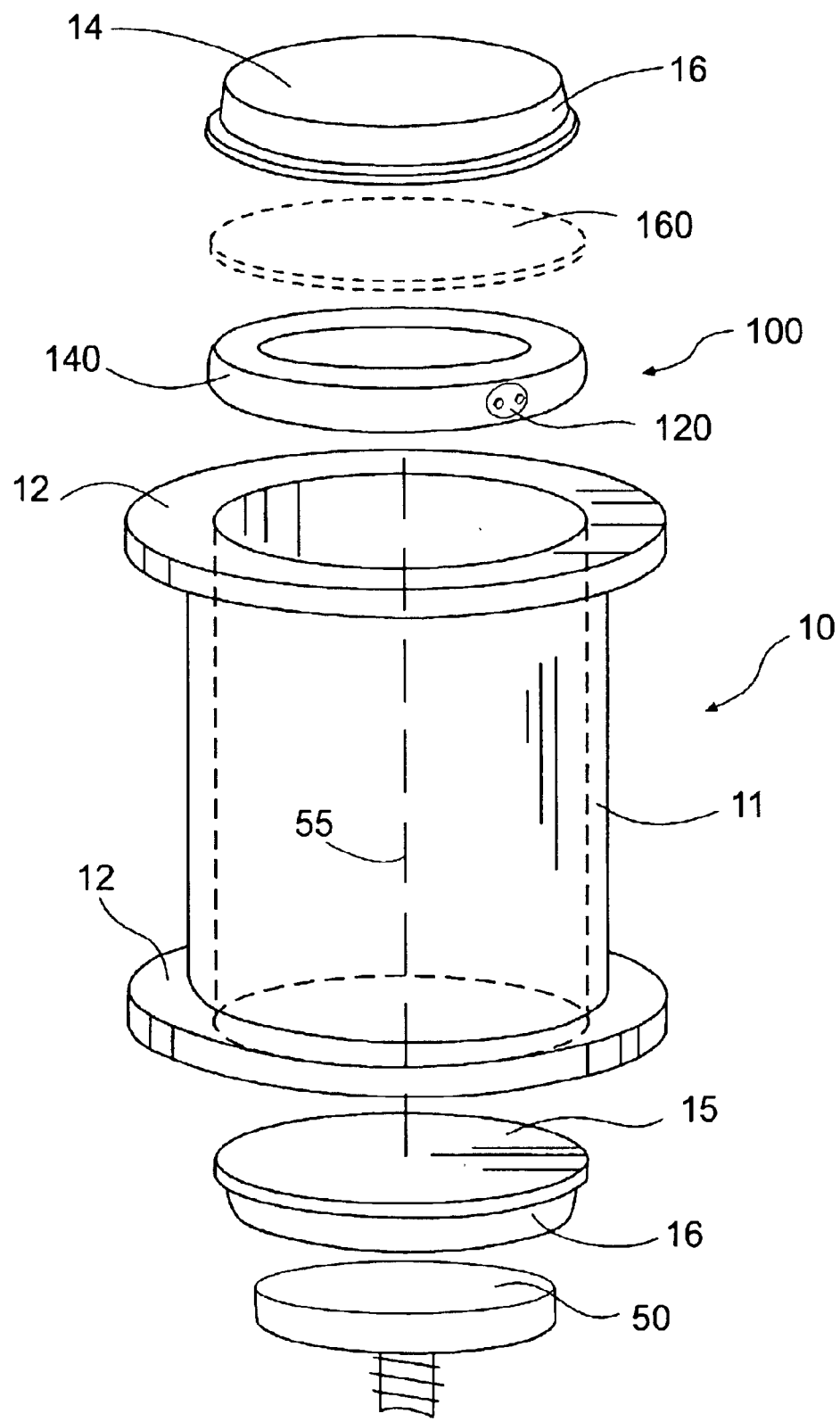
FIG. 1 is an exploded perspective view of a mold assembly for a gyratory compactor having an apparatus for dynamically measuring the gyratory angle of the mold, according to one embodiment of the present invention.
Figure 2:
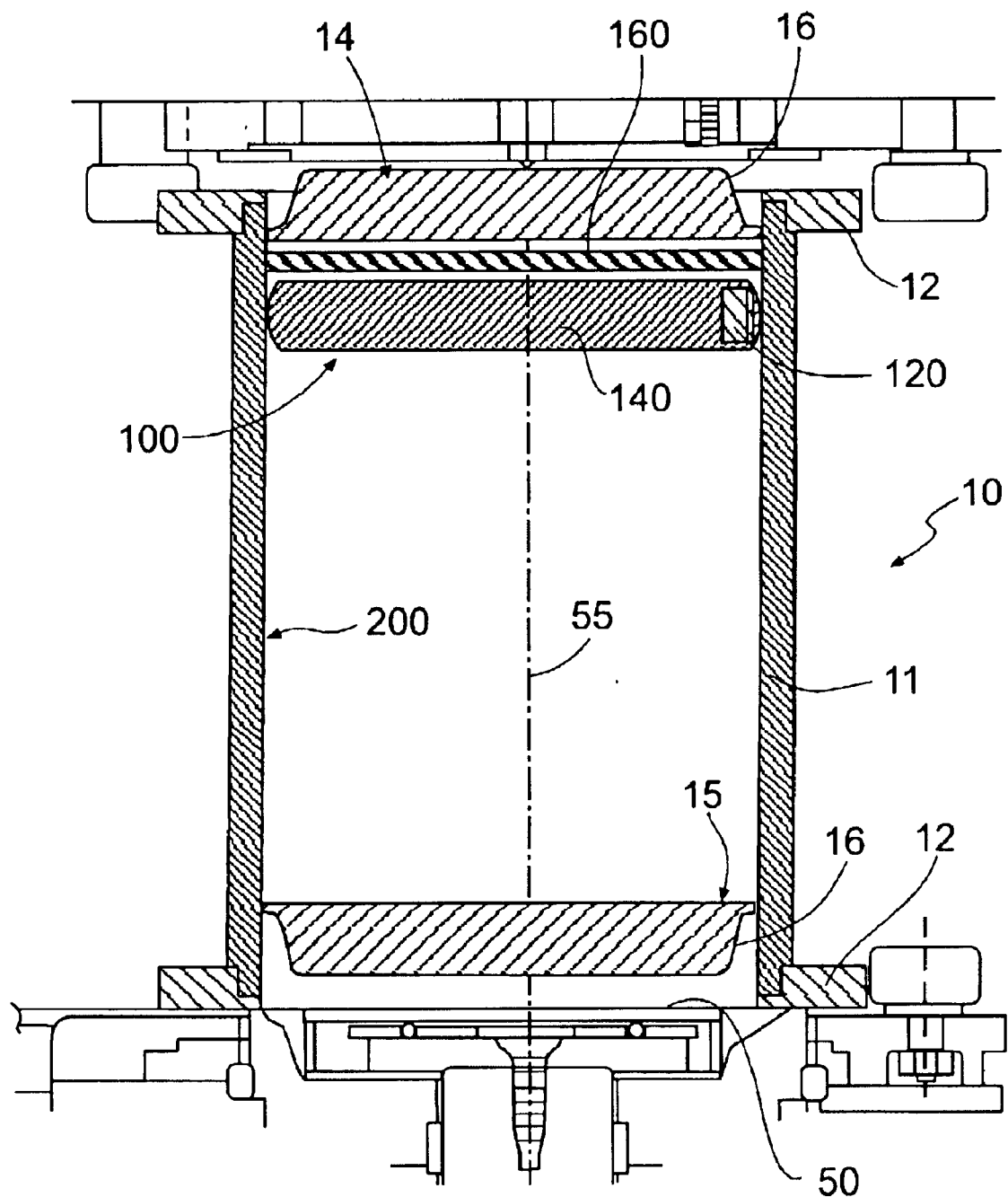
FIG. 2 is a cross-sectional view of a mold assembly for a gyratory compactor having an apparatus for dynamically measuring the gyratory angle of a mold, according to one embodiment of the present invention, and installed in a gyratory compactor.

FIGS. 1 and 2 illustrate a gyration angle measurement system according to one embodiment of the present invention, the system being particularly adapted for use with a Superpave gyratory compactor of the type described. In FIG. 1, a cylindrical mold 10 is configured to produce a cylindrical test sample from a sample of asphalt paving mix. The mold 10 includes a cylindrical side wall 11 which is of a substantially uniform inner diameter and has open opposite ends. The particular mold 10 illustrated in FIG. 1 has out-turned flanges 12 adjacent to the upper and lower ends of the cylindrical side wall 11 which provide engagement surfaces cooperating with components of one particular design of a commercially available gyratory compactor apparatus so that the gyratory compactor apparatus can hold the mold 10 and impart a gyratory motion thereto. However, some gyratory compactor designs do not require a flanged mold 10. Therefore, it should be clearly understood that the flanges 12 shown in FIG. 1 are not an essential part of the present invention, and the present invention can be operated with other mold designs, including those having a single flange or having no flange, or having other auxiliary elements provided on the mold to cooperate with a particular design of gyratory compactor.

During the compaction process, the open opposite ends of the mold 10 are closed by removable disk-shaped plates 14, 15, otherwise referred to as "disks" or "pucks", so that pressure can be applied to the sample of asphalt paving mix located within the mold 10 between the plates 14, 15. More particularly, a compaction ram 50 is urged into the mold 10 along the longitudinal axis thereof, while the sample is simultaneously subjected to a rotating shear force resulting from the gyration of the mold 10 about the longitudinal axis with a specified tilt angle or angle of gyration, and without rotation of the mold 10 with respect to the axis. Certain of the commercially available gyratory compactor designs employ two separate and independent plates 14, 15 which are not physically connected to any part of the gyratory compactor apparatus, and this is the design shown in the accompanying drawings. In other designs (not shown) the end of the compaction ram 50 of the compactor functions as one of the disk-shaped plates 14, 15. However, embodiments of the present invention are applicable to both of these variations. Further, as will be apparent from the discussion herein, the ram pressure and displacement, the gyration angle, the gyration rate, and the total number of gyrations are exemplary critical parameters in the operation of the gyratory compactor apparatus.

As shown in FIGS. 1 and 2, the plates 14, 15 have an outer diameter corresponding substantially to the inner diameter of the mold 10 so as to fit loosely within the mold 10 without binding. Preferably, the plates 14, 15 have a tapered outer wall 16 to accommodate the tilting and gyrating movement of the mold 10. Typically, during normal use, when the gyratory compactor apparatus is used for producing test samples, one plate 15 is placed within the mold 10 to block one end thereof and then a measured sample of the asphalt paving mix is introduced into the mold 10. The opposite end of the mold 10 is closed by placing the second plate 14 within the mold 10 and then the assembly is placed within a gyratory compactor apparatus. Once placed into the compactor apparatus, the plate 14 at one end of the mold 10 is supported or restrained, while a pressure ram 50 is moved into position bearing against the opposite plate 15 to apply a compaction pressure to the sample within the mold 10. As the pressure is being applied, the mold 10 is gyrated about an angle of gyration, in accordance with well-known techniques, for example, as disclosed in the aforementioned patents. For those designs of gyratory compactors which use only a single plate, rather than a pair of plates, the mold is positioned in the gyratory compactor and either the pressure ram itself, or else a plate carried by the ram, is brought into position for applying pressure to the sample.

As previously discussed, gyratory compactors typically have an angle of gyration which is a parameter of the design and construction of the machine, wherein the angle is usually set and calibrated during initial manufacture and then periodically checked and reset if necessary. The force applied by the pressure ram may also be initially calibrated and then periodically verified in a static mode with, for example, a load cell. However, the gyration angle may vary dynamically during the operation of the gyratory compactor. Further, the control system of the gyratory compactor, and/or the pressure ram itself, may not hold the pressure within the required specifications throughout the entire compaction process since the compaction process is a dynamic process where the mold is constantly gyrated while pressure is applied. Also, the sample within the mold is reduced in height as it is compacted which, along with other factors, can affect the actual pressure dynamically applied to the sample by the gyratory compactor. As such, an out-of-specification gyration angle or compaction pressure may often not be discovered until the periodic check of the machine, thereby presenting a risk of extensive invalid test results since Superpave gyratory compactor specifications call for the mold 10 to be gyrated at a specified angle, at a specified rpm, and while applying a specified constant pressure.

As such, embodiments of the present invention provide a monitoring apparatus 100 having one or more sensing devices 120 incorporated into a rigid disk-shaped plate 140. As shown in FIGS. 1 and 2, the apparatus 100 is inserted into the mold 10 so as to be adjacent to either of the plates 14, 15 or the compactor ram 50. The sample of the asphalt paving mix is disposed between the two plates 14, 15 or between one of the plates 14, 15 and the compactor ram 50, as previously described. Accordingly, depending on the particular configuration, the apparatus 100 may or may not be in direct contact with the sample. Though the monitoring apparatus 100 is described herein as being separate from the plates 14, 15 and the compactor ram 50, it will be understood by one skilled in the art that the monitoring apparatus 100 could, in some instances, be incorporated into any or all of the compactor ram 50 and the plates 14, 15. As will be described further below, some embodiments of the present invention may also require that a spacer 160, in some instances comprised of a non-magnetic material, be disposed between the apparatus 100 and either of the plates 14, 15 or the compactor ram 50. The spacer 160 may, in some instances, be a separate component or, in other instances, may be integrally-formed with any of the apparatus 100, the plates 14, 15, or the compactor ram 50.

According to one advantageous embodiment of the present invention, the apparatus 100 may be configured so as to be capable of determining the gyration angle of the mold 10. Such an apparatus 100 is typically configured such that the plate 140 remains perpendicular to the ram axis 55 of the gyratory compactor during the compaction process, as is also generally required of the plates 14, 15. Further, the sensing device 120 is configured with respect to the plate 140 so as to measure a proximity of a reference member 200 with respect to the sensing device 120, as described below, wherein, when the apparatus 100 is configured to measure the gyration angle of the mold 10, the reference member 200 comprises the mold 10 itself. Each sensing device 120 is further configured to provide an output signal corresponding to the proximity of the reference member 200 with respect to the sensing device 120. The output signal can thereafter be correlated with the parameter being measured. For example, one or more sensing devices 120 may be configured with respect to the plate 140 such that the proximity of the mold 10 (reference member 200) with respect to each sensing device 120, as determined from the signals produced by the sensing devices 120, may be monitored during the entire cycle of operation of the gyratory compactor apparatus, in both static and dynamic modes. In an appropriately configured apparatus 100, the signals produced by the sensing devices 120 may be correlated so as to indicate the actual gyration angle of the mold 10.

Preferably, the one or more sensing devices 120 are configured to accomplish the necessary proximity measurements without contacting the reference member 200. The benefits of a non-contacting sensing device 120/reference member 200 system will be readily appreciated by one skilled in the art. For example, a non-contacting sensing device 120 will not be affected by accretions on the reference member 200, and a non-contacting sensing device 120/reference member 200 system will not be prone to wear of either of the sensing device 120 or reference member 200 components. Accordingly, the measurements will be more accurate and measurement calibration is more readily maintained. However, though the present invention is described herein in terms of a non-contacting sensing device 120/reference member 200 system, the reference member 200 may, in some instances, contact the sensing device(s) 120, if such contact is necessary and the aforementioned shortcomings of a contacting system can be avoided.

An appropriate sensing device 120 according to the present invention is preferably configured to be non-contacting with respect to the reference member 200 and capable of determining the proximity of the reference member 200 with respect thereto. Such a sensing device 120 may comprise, for example, a Hall-effect or magnetoresistive effect transducer, each configured to be responsive to a magnetic flux. However, the sensing device 120 may also or alternatively comprise, for instance, a magnetic sensor, an accelerometer device, an electro-optical device, an inductive/capacitive device, any other suitable type of proximity sensor, or combinations of any appropriate sensors. Accordingly, though embodiments of the present invention will be described in terms of a Hall-effect type sensor, it will be understood by one skilled in the art that embodiments of the present invention may also be accomplished with various other types of sensors using the principles as disclosed herein.

Hall-effect transducers, in some common applications, are configured to measure a magnetic field and to produce a corresponding voltage signal, wherein such Hall-effect transducers will be appreciated by one skilled in the art. Basically, the Hall effect occurs when an applied magnetic field deflects charge carriers in a conductor or semiconductor material, causing a difference in electrical potential across the side of the material that is transverse to the magnetic field and the current direction. The magnitude of the Hall-effect voltage is proportional to the strength of the magnetic field applied to the transducer. Thus, according to particularly advantageous embodiments of the present invention, an appropriate apparatus 100 may comprise, for example, one or more ferromagnetic Hall-effect transducers comprising the sensing device(s) 120, incorporated within the plate 140. The plate 140, in turn, may then be placed into the mold 10 in such a manner as to be capable of determining the orientation of the plate 140 with respect to the inside surface of the mold 10 (reference member 200), since the mold 10 is typically comprised of a ferromagnetic material. The resulting orientation of the plate 140 with respect to the mold 10 thereby corresponds to the angle of gyration of the mold 10. When incorporated in such a manner, the apparatus 100 may be used as an integral part of the mold 10 or the gyratory compactor during the compaction process so as to permit continuous measurement of the gyration angle. In such instances, the gyratory compactor may also be configured to be responsive to the gyration angle determined by the apparatus 100, wherein the gyration angle may be automatically controlled and adjusted to provide the desired or required gyration angle, as will be appreciated by one skilled in the art. Alternatively, the apparatus 100 may be employed as a stand-alone angle calibration device applicable to existing gyratory compactors to permit independent measurement of the gyration angle.

Figure 3A:
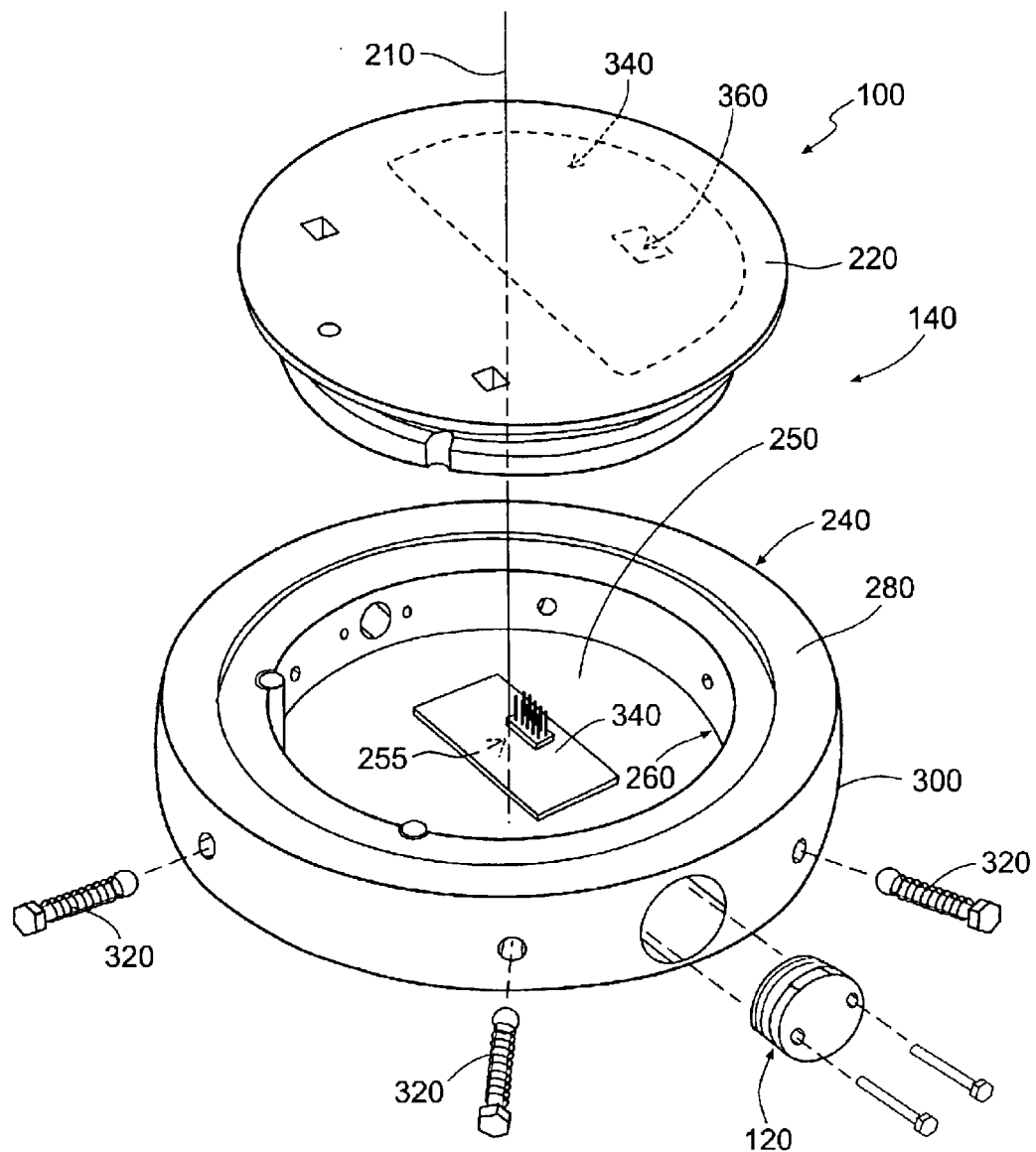
FIG. 3A is an exploded perspective view of an apparatus adapted to dynamically measure the gyratory angle of a mold for a gyratory compactor according to one embodiment of the present invention.

As shown in FIG. 3A, the plate 140 may be configured as a circular plate having a longitudinal axis 210 and comprising a cover 220 configured to engage a housing 240. The housing 240 is generally a hollowed out structure having a circular base portion 250 defining a center 255 and a periphery 260. A ring portion 280 extends from the periphery 260 of one face of the base portion 250 coaxially with the center 255. The outer edge of the ring portion 280 and the periphery 260 of the base portion 250 further cooperate to form a radiused edge 300 for allowing the apparatus 100 to remain perpendicular to the ram axis 55 as the mold 10, and such that the apparatus 100 does not bind in the mold 10, as the mold 10 is gyrated. The cover 220 is configured to engage the housing 240 so as to be securely retained and to form a flush surface with the ring portion 280. As shown, in one embodiment, one or more spring-loaded detent ball mechanisms 320 can be configured to interact between the cover 220 and the housing 240 so as to provide a suitable securing mechanism while still allowing the cover 220 to be removed when necessary. However, one skilled in the art will also appreciate that many other mechanisms may be used to removably secure the cover 220 with respect to the housing 240. Since advantageous embodiments of the present invention, as described herein, implement a magnetic-type effect, the housing 240 and the cover 220 are preferably comprised of non-magnetic materials so as to minimize or eliminate interference between the sensing device(s) 120 and the reference member 200. Accordingly, a non-magnetic spacer 160, as previously discussed, may also be disposed adjacent to or be formed integrally with the apparatus 100 so as to minimize or eliminate interference from either plate 14, 15 or the compactor ram 50.

In one advantageous embodiment where the apparatus 100 is configured to measure the gyration angle of the mold 10, one or more sensing device(s) 120 may be incorporated into the plate 140 in the outer radiused edge 300 of the apparatus 100 such that each sensing device 120 is disposed adjacent to, but spaced apart from, the inner side wall 11 when the apparatus 100 is inserted into the mold 10. In some instances, the sensing device(s) 120 may be recessed into the outer radiused edge 300 of the apparatus 100 in order to provide the desired spaced apart relation of the sensing device 120 and the inner side wall 11. As previously described, each sensing device 120 is configured to provide an output signal representative of the proximity of the reference member 200 with respect thereto, wherein, in some embodiments, the reference member 200 comprises the mold 10 and the output signal represents the actual gyration angle of the mold 10. As such, the apparatus 100 further comprises electronic circuitry 340 in communication with the sensing device(s) 120, wherein the electronic circuitry 340 is configured as a receiver to, for example, sample or otherwise receive the output signal from the sensing device(s) 120 and/or convert the output signal into a corresponding digital or analog data.

In some instances, the electronic circuitry 340 may preferably also comprise a receiver component (not shown) configured to store the data such that, where provisions are included in the electronic circuitry 340 for allowing a computer device (not shown) to be interfaced therewith, the data can be read or otherwise received by the computer device following the compaction process after the apparatus 100 has been removed from the mold 10. More particularly, for example, the data may be stored within an electronic nonvolatile memory for subsequent download after the completion of a given compaction process. In other instances, the apparatus 100 may also comprise a receiver/transmitter 360 in communication with the electronic circuitry 340 and capable of receiving and transmitting the data corresponding to the output signal(s) to, for example, a computer device (not shown) or other indicia or device capable of displaying the data such as, for instance, an appropriately configured LED or LCD. In one embodiment, the receiver/transmitter 360 may be configured to wirelessly transmit the data and may comprise, for example, an ultrasonic wireless data transmission system or a radio frequency data transmission system. However, in other instances, the receiver/transmitter 360 may be configured to transmit the data through a wireline (not shown) or by another appropriate mechanism. In some such instances, the data may be transferred from the apparatus 100 in real time. However, one skilled in the art will appreciate that the apparatus 100 may be configured to and/or may include other components for allowing the extraction of the output signal(s) or the corresponding data.

Figure 3B:
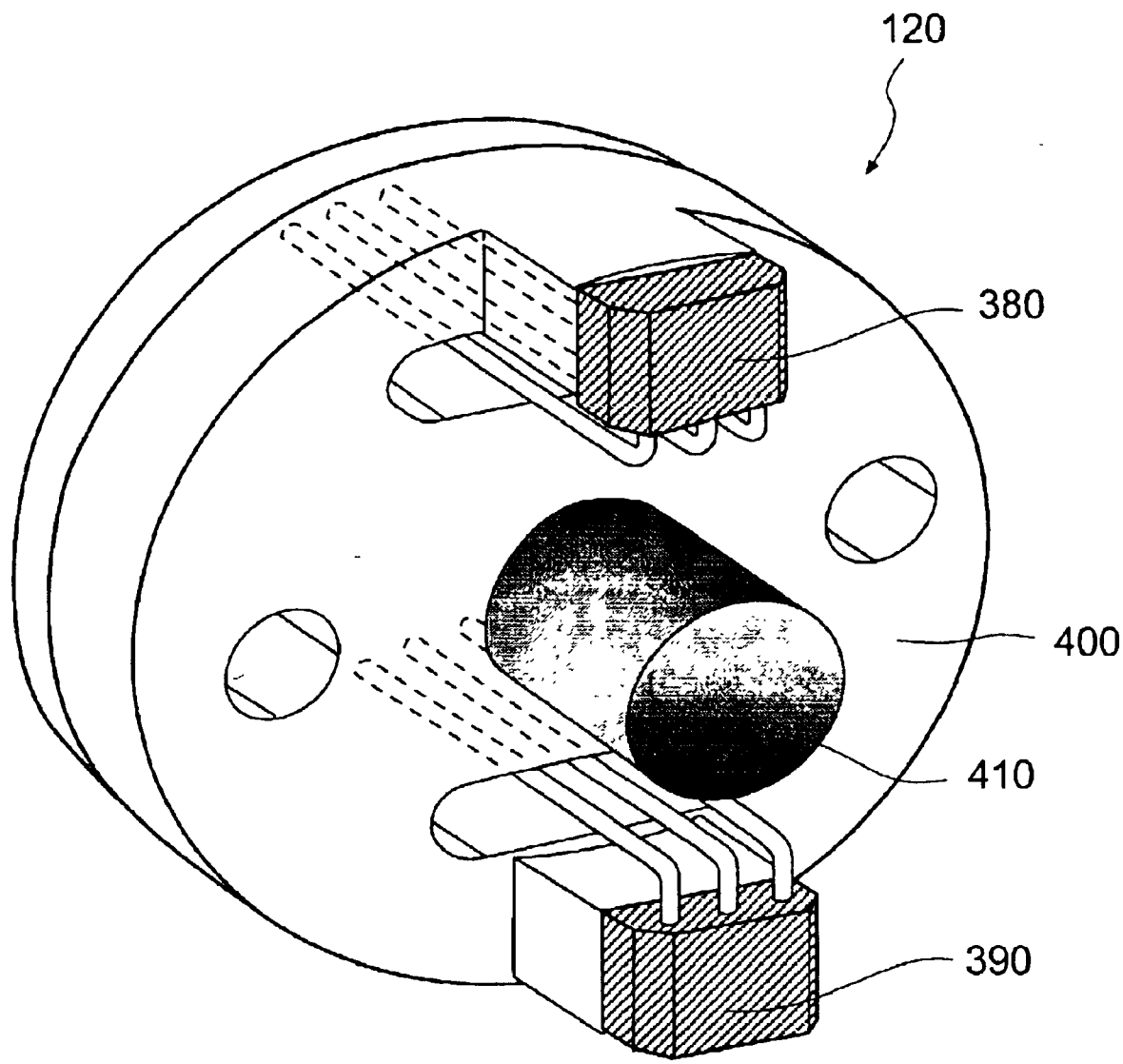
FIG. 3B is a perspective assembled view of a sensing device component of an apparatus adapted to dynamically measure the gyratory angle of a mold for a gyratory compactor according to one embodiment of the present invention.

As more particularly shown in FIG. 3B, one embodiment of a sensing device 120 for determining the angle of gyration according to the present invention comprises a pair of Hall-effect transducers 380, 390 mounted in diametrically opposed and evenly-spaced positions with respect to a soft ferromagnetic and radially-symmetric housing 400. A permanent magnet 410 is disposed about the center of the housing 400. Accordingly, in free space or in the absence of a nearby ferromagnetic metal mass, the distribution of the flux density from the magnet 410 will be radially symmetric and the transducers 380, 390 will experience equal magnitudes of magnetic flux. As such, when the sensing device(s) 120 is/are mounted in the plate 140 of the apparatus 100 and the apparatus 100 is disposed in the mold 10 such that the transducers 380, 390 are oriented toward the ferromagnetic inner side wall 11 and parallel with the axis of the mold 10, the transducers 380, 390 will experience substantially equal magnitudes of magnetic flux due to even spacing with respect to the inner side wall 11. That is, the transducers 380, 390 oriented in parallel with the axis of the mold 10 will experience substantially equal magnitudes of magnetic flux only when the axis of the apparatus 100 is oriented in parallel with the axis of the cylindrical mold 10 such that the lateral plane of the apparatus 100 is perpendicular to the inner side wall 11.

Figure 3C:
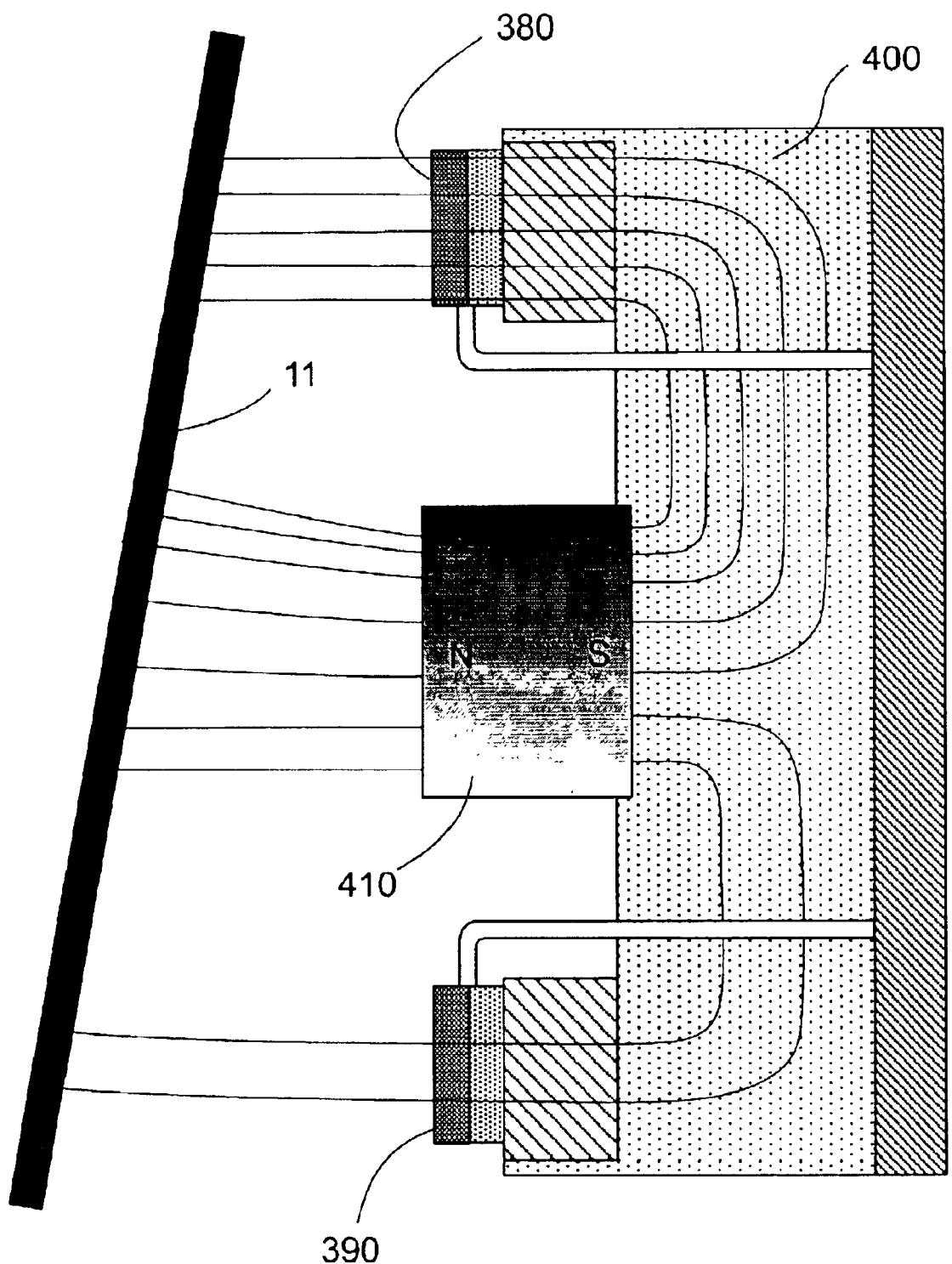
FIG. 3C is a schematic of a sensing device component of an apparatus adapted to dynamically measure the gyratory angle of a mold for a gyratory compactor, according to one embodiment of the present invention, illustrating the interaction of the sensing device component with the wall of the mold.

Thereafter, in the described configuration, if the lateral plane of the apparatus 100 is tilted or angled with respect to the inner side wall 11, one transducer 380 moves closer to the inner side wall 11 while the other transducer 390 moves further away, as shown in FIG. 3C. That is, the transducers 380, 390 are arranged such that an increase in the magnetic field strength experienced by the transducer 380 closer to the inner mold side 11 is accompanied by a decrease in the magnetic field strength experienced by the transducer 390 further from the inner side wall 11. The transducers 380, 390 are initially calibrated to indicate substantially equal values of magnetic field strength when the lateral plane of the apparatus 100 is perpendicular to the inner side wall 11. Thus, according to the described mechanism, the magnetic flux experienced by each transducer 380, 390 varies as a function of the angle between the lateral plane of the apparatus 100 and the inner side wall 11. As such, when the mold 10 is gyrated during the compaction process, the mold 10 moves with respect to the apparatus 100, wherein the apparatus 100 is configured to remain perpendicular to the ram axis 55 of the gyratory compactor during the compaction process, such that the transducers 380, 390 alternate between a more proximate and a less proximate position with respect to the inner side wall 11.

One skilled in the art will also appreciate that, as a result of the described configuration, the transducers 380, 390 are capable of emitting therefrom a signal indicative of the gyration angle of the mold 10. More particularly, the gyration of the mold 10 is sensed as a proximity measurement by the transducers 380, 390, each of which thereby produces an alternating voltage output signal. The absolute value of the difference in amplitude between the voltage output signals of the transducers 380, 390 at any instance during the gyration process thus corresponds to a real time measurement of the angle of gyration with respect to the inner side wall 11. Further, in one advantageous embodiment of the present invention, an apparatus 100 configured to determine the angle of gyration includes two sensing devices 120 installed in the radiused edge 300 of the apparatus 100 in a diametrically-opposed relationship. Such a configuration may be implemented where, for example, due to wear or original tolerances between the apparatus 100 and the inner side wall 11, the proximity of each sensing device 120 with respect to the inner side wall 11 may not be consistent throughout the compaction process as the mold 10 is gyrated. As such, using the diametrically-opposed sensing devices 120, the output signals of the two sensing devices 120 may be monitored and averaged so as to account for any gaps or "play" between the apparatus 100 and the inner side wall 11. The voltage output signals from the transducers 380, 390 may then be received, stored, processed, and/or transmitted by the associated electronic circuitry 340, as previously described.

According to the description of embodiments of the present invention as provided herein with respect to devices, apparatuses and systems for determining the gyration angle, it will be understood that the disclosure further supports a method of determining a gyration angle of an open-ended cylindrical mold for a gyratory compactor. For example, such a method may first comprise inserting at least one sensing device into an open end of a mold having a wall defining an inner diameter, wherein the at least one sensing device is operably engaged with a rigid disk-shaped plate defining an axis and having a diameter corresponding substantially to the inner diameter of the mold. In such instances, the at least one sensing device is disposed about a periphery of the plate so as to be spaced apart from and cooperable with the wall when the plate is disposed within the mold. A signal is then received from the at least one sensing device, wherein the signal corresponds to the angle of the wall with respect to the axis of the plate as dynamically determined by the at least one sensing device as the mold is being gyrated. Accordingly, such a signal would thereby be indicative of the gyration angle of the mold.

Figure 4A:
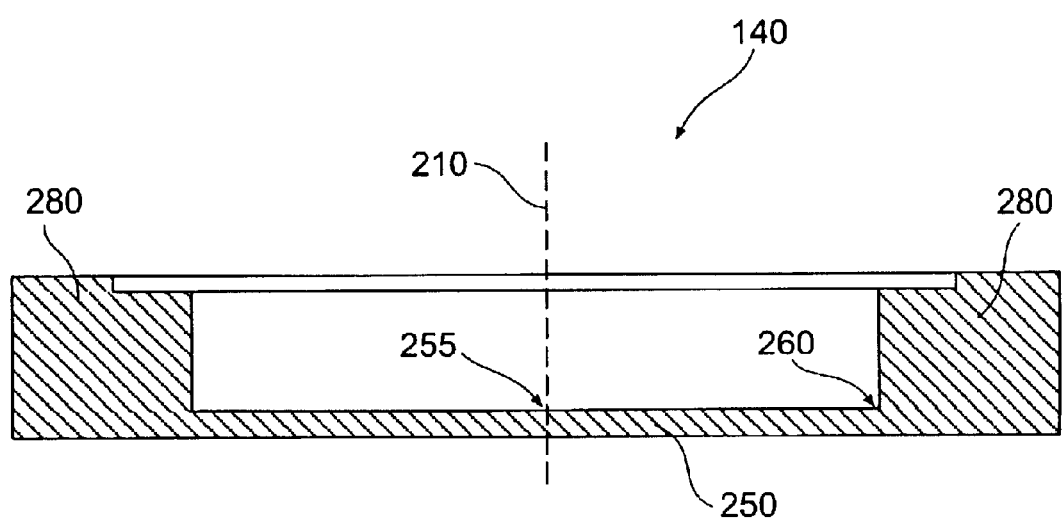
FIG. 4A is cross-sectional schematic of a housing of an apparatus adapted to dynamically measure the pressure exerted on a sample within a mold in a gyratory compactor according to one embodiment of the present invention.
Figure 4B:
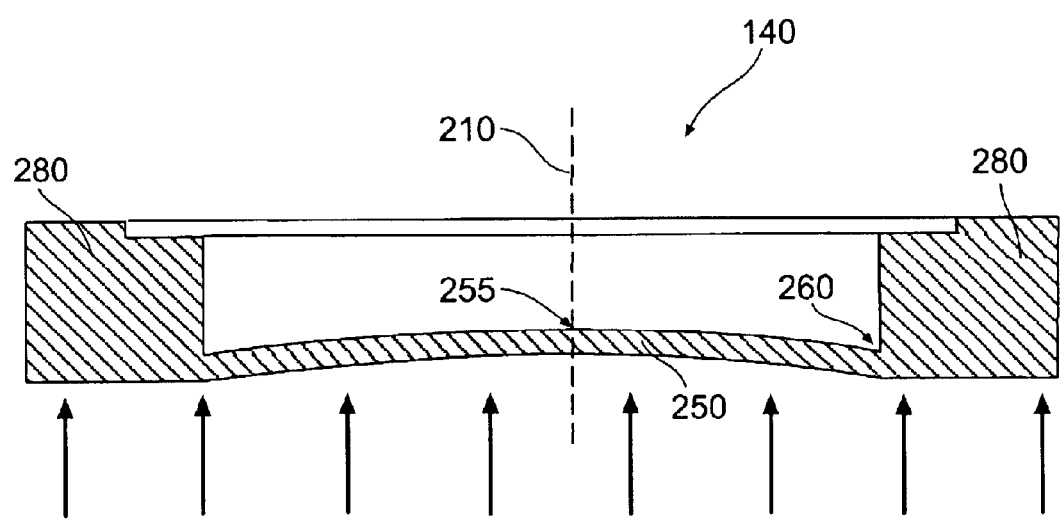
FIG. 4B is a cross-sectional schematic of a response to an exerted pressure of a housing of an apparatus adapted to dynamically measure the pressure exerted on a sample within a mold in a gyratory compactor according to one embodiment of the present invention.
Figure 4C:
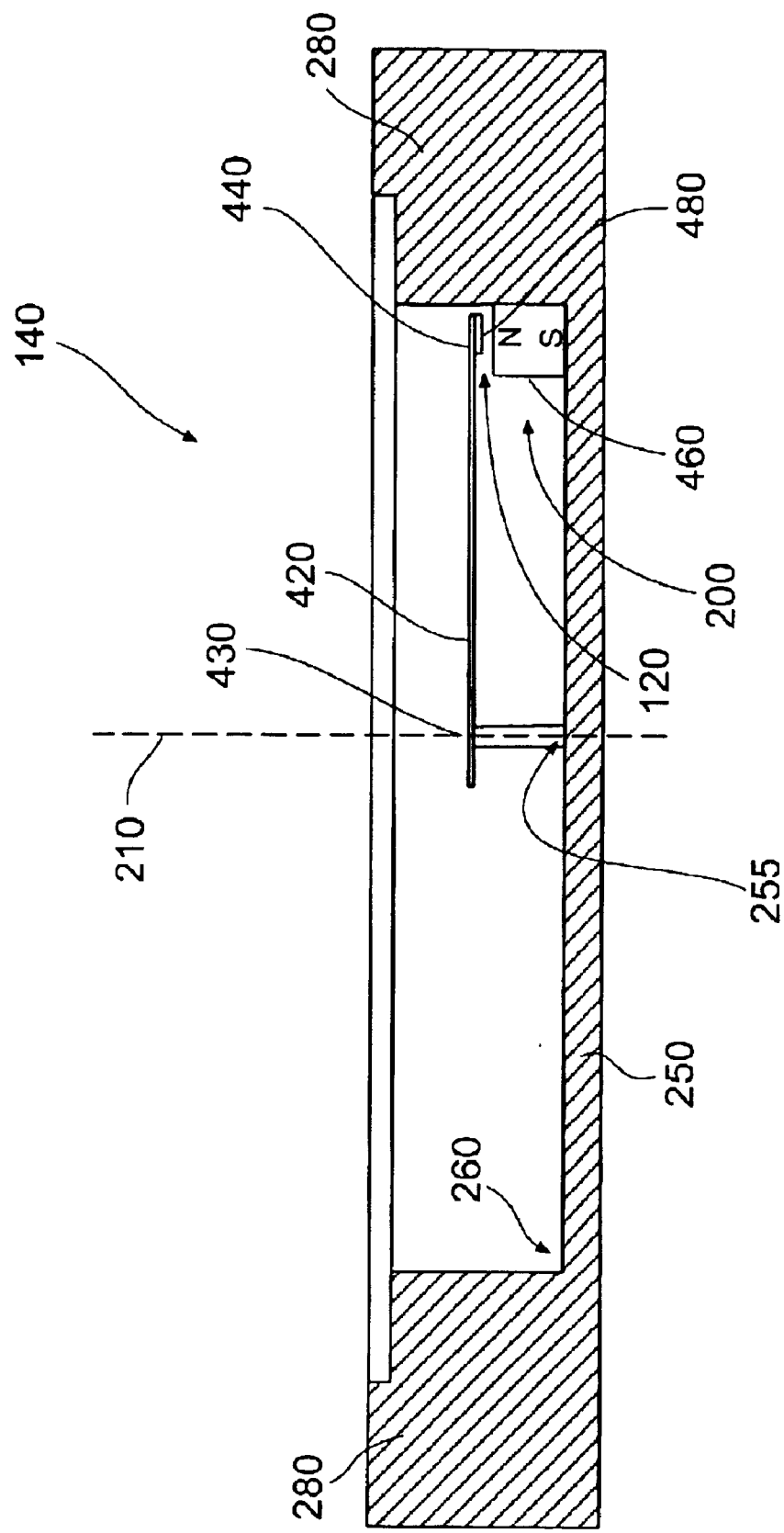
FIG. 4C is a cross-sectional schematic of an apparatus for dynamically measuring the pressure exerted on a sample within a mold in a gyratory compactor, according to one embodiment of the present invention, illustrating the interaction of the proximity-sensing device component with a reference member mounted in the housing.

Another advantageous aspect of the present invention comprises a monitoring apparatus 100 configured to determine the pressure applied to the sample of asphalt paving mix disposed within the mold 10 during the compaction process, as shown in FIGS. 4A–4C, using a plate 140 having a housing 240 and corresponding cover 220, as previously described. Such an apparatus 100 may utilize a housing 240 as described above and as shown in FIG. 4A, having a hollowed out structure with a circular base portion 250 and a ring portion 280 extending from the periphery 260 of the base portion 250. As such, one skilled in the art will appreciate that, where the ring portion 280 is axially supported and a pressure is exerted across the face of the base portion 250 opposite the ring portion 280, the unsupported center 255 will experience a deflection as a result of the pressure, while the supported periphery 260 about the ring portion 280 will experience little, if any, deflection, as shown in FIG. 4B. (See, e.g., Table 24, Case 10b of Young, Warren C., *Roark's Formulas for Stress and Strain*, $6^{th}$ Ed., 1989, McGraw-Hill Publishers).

Based upon the aforementioned effect and as shown in FIG. 4C, the apparatus 100 may further comprise a bar 420 mounted at the center 255 and extending toward the ring portion 280 about the periphery 260. In one embodiment, the bar 420 is nonmagnetic and may be, for example, a separate component or an extension of the circuit board on which the electronic circuitry 340 is mounted. The bar 420 includes a mounting point 430 about the center 255 and a distal end 440 at which the bar 420 ends. At least one sensing device 120 is mounted to the distal end 440 of the bar 420. A reference member 200 comprising, according to one embodiment, a permanent magnet 460, is mounted on the base portion 250 toward the ring portion 280 and about the periphery 260, so as to be in a position adjacent to the sensing device(s) 120. The bar 420 is further configured such that a deflection of the center 255 along the axis 210 of the plate 140 results in corresponding and equal displacements of both the mounting point 430 and the distal end 440 of the bar 420 along the axis 210.

According to one embodiment, the sensing device 120 may comprise, for example, a Hall-effect transducer 480, as previously described, mounted to the bar 420. However, in some instances, more than one Hall-effect transducer may be used. In still other instances, the bar 420 may extend through the center 255 toward diametrically-opposed points about the periphery 260 such that a sensing device 120 on each end thereof is in correspondence with two reference members 200 disposed in diametrical opposition on the base portion 250 adjacent to the ring portion 280. The output signals from the sensing device(s) 120 correspond to the relative proximity of the reference member 200 with respect to the sensing device(s) 120, as the center 255 is deflected by an applied pressure. Accordingly, the output signals from the sensing device(s) 120 can be correlated with and are representative of the actual pressure conditions that exist within the mold 10 and thus the pressure exerted on the sample during the entire cycle of operation of the compactor apparatus, in both static and dynamic modes. Though embodiments of the present invention for measuring the pressure exerted on the sample are described in terms of a Hall-effect type sensor, it will be understood by one skilled in the art that embodiments of the present invention may also be accomplished with various other types of sensors as discussed above and using the principles as disclosed herein.

The various forms of sensing devices 120 disclosed herein for use with the various embodiments of the present invention may, in some instances, be affected by temperature gradients experienced by the mold 10 in the gyratory compactor during the compaction process. Such temperature gradients, during a single test, may be as large as 280° F., with temperatures ranging from about 20° F. to 300° F. Accordingly, a monitoring apparatus 100 according to the present invention may further be configured to measure or monitor the temperature experienced by the sensing device (s) during the compaction process, wherein the measured temperatures may be input into, for example, a temperature compensation circuit, so as to compensate or adjust for changes in output signals of the sensing device(s) 120 due to the temperature changes.

Further, in some instances, it may also be advantageous for the embodiments of the present invention to include a device 500 for calibrating the monitoring apparatus 100. For example, where the monitoring apparatus 100 is configured to measure the angle of gyration, the calibration device 500 may comprise, as shown in FIG. 5A, a first cylindrical tube 520 having an inner diameter slightly larger than the diameter of the plate 140, and a base 540, wherein calibration device 500 is formed such that the plane of the base 540 is perpendicular to the axis of the first tube 520. The calibration device 500 would also comprise a second cylindrical tube 560 also having a base 580. However, the plane of the base 580 would be configured to be disposed at a desired angle with respect to the axis of the second tube 560. For example, for a horizontally-disposed plane of the base 580, the axis of the second tube 560 would be disposed at an angle 0 of 1.25 degrees from vertical, in conformance with the Superpave gyratory compactor specifications. Accordingly, when inserted into the second tube 560, each sensing device 120 of the apparatus 100 would provide a certain output signal corresponding to the 1.25 degree angle, as previously described. The same monitoring apparatus 100 thereafter inserted into the first tube 520, if properly calibrated, should then provide output signals from the sensing devices 120 indicating no magnetic flux differentials, as also previously described.

Another configuration of a calibration device is illustrated in FIG. 5B and indicated generally by the numeral 600. According to such an embodiment, a precision flat 620 comprised of, for example, granite, provides a flat surface on which the monitoring apparatus 100 is placed. A tubular member 640 is sized to have an inner diameter corresponding to the diameter of the mold 10. One end 650 of the tubular member 640 is configured to be perpendicular to the axis 660 thereof, while the other end 670 of the tubular member 640 is cut at an angle $\theta$, such as, for example, 1.25 degrees, from perpendicular to the axis 660 of the tubular member 640. Accordingly, the flat end 650 of the tubular member 640 may be placed over the plate 140 and in contact with the precision flat 620 so as to verify an output signal from the apparatus 100 corresponding to no magnetic flux differential. The tubular member 640 can then be removed and turned over such that the angled end 670 is placed over the plate 140. The output signal from the apparatus 100 corresponding to the 1.25 degree angle can then be verified. Such calibration devices 500, 600 could, for example, be readily verified as providing NIST-certifiable results and would also be a simple, inexpensive, and expeditious manner of checking and maintaining calibration of the gyratory compactor device.

One skilled in the art will also appreciate, from the disclosure herein, that a calibration device for a monitoring apparatus 100 configured to determine the pressure exerted on the sample may also be provided. For example, the pressure-sensing monitoring apparatus 100 will show a certain output signal from the sensing device(s) when no pressure is exerted on the plate 140. Accordingly, a known pressure exerted on the apparatus 100 will also produce a certain output signal whereafter, once the known pressure is removed from the apparatus 100, the sensing device(s) 120 should return to providing the output signal indicating no pressure on the plate 140.

Further, one skilled in the art will also appreciate that various embodiments discussed herein may, in some instances, be combined into a single monitoring apparatus 100. For example, a monitoring apparatus 100 may be configured to determine the angle of gyration, the pressure experienced by the sample during the compaction process, and/or the temperature of the sample during the compaction process for correcting or adjusting the data collected from the sensing device(s) 120. More particularly, in one instance, a monitoring apparatus 100 may be configured to determine the angle of gyration, as discussed above, but may also include sensing device(s) 120 mounted on a bar 420, adjacent to a reference member 200, as discussed with respect to the configuration for measuring the pressure experienced by the sample. However, if such a combination apparatus 100 is configured to implement, for example, a magnetic-type sensing device 120 such as a Hall-effect transducer, the apparatus 100 must also be configured to minimize interference between the different mechanisms. For instance, the bar-mounted sensing device(s) 120 mechanism for determining pressure may be oriented perpendicularly or at a lesser angle to the sensing devices 120 used to determine the gyration angle. In other instances, for example, magnetic shielding (not shown) may be included within the plate 140 for appropriately isolating the different mechanisms, as will be appreciated by one skilled in the art.

Many modifications and other embodiments of the invention will come to mind to one skilled in the art to which this invention pertains having the benefit of the teachings presented in the foregoing descriptions and the associated drawings. For example, the monitoring apparatus 100 may also be configured to monitor additional parameters within the mold 10 or associated with the asphalt paving mix during the compaction process. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A device adapted to dynamically measure a pressure exerted on a sample contained within a cylindrical mold or a gyratory compactor, said device comprising:
   a rigid disk-shaped plate defining an axis and a periphery, the plate being adapted to be disposed within the mold in communication with the sample; and
   at least one proximity-sensing device operably engaged with the plate, the at least one proximity-sensing device being configured to dynamically measure a proximity of a reference member with respect to the at least one proximity-sensing device and to produce therefrom a signal corresponding to the pressure exerted on the sample within the mold.

2. A device according to claim 1 wherein the plate further comprises a disk-shaped base portion having a center and opposing faces and a ring-shaped portion coaxial with the center and extending from the periphery of one of the faces, the center being configured to experience a deflection with respect to the periphery in response to pressure applied across the other face of the base portion.

3. A device according to claim 2 wherein the reference member is disposed on the base portion of the plate, away from the center and adjacent to the ring-shaped portion, and wherein the at least one proximity-sensing device is mounted on a distal and of an arm adjacent to the reference member, the arm having a proximal end mounted at the center and extending to the distal end substantially parallel to the base portion, the deflection of the center in response to pressure resulting in a corresponding displacement of the arm and the at least one proximity-sensing device parallel to the axis, the reference member being configured with respect to the at least one proximity-sensing device such that the displacement of the arm parallel to the axis and away from the reference member is sensed by the at least one proximity-sensing device, the corresponding signal produced by the at least one proximity-sensing device thereby being indicative of the pressure exerted on the sample within the mold.

4. A device according to claim 3 wherein the at least one proximity-sensing device further comprises at least one magnetic flux-sensitive transducer.

5. A device according to claim 4 wherein the reference member a comprises a permanent magnet.

6. A device according to claim 1 wherein the at least one proximity-sensing device is selected from the group consisting of a Hall effect transducer, a magnetoresistor, a magnetic sensor, an accelerometer device, an electro-optical device, an inductive/capacitive device, a proximity sensor, and combinations thereof.

7. A device according to claim 1 further comprising a receiving unit configured to receive the signal from the at least one proximity-sensing device and to provide an indicia of the pressure exerted on the sample within the mold.

8. A device according to claim 1 further comprising a receiving unit operably engaged with the plate and configured to receive the signal from the at least one proximity-sensing device and to store the signal in a computer-readable manner.

9. A device according to claim 1 further comprising a receiving unit remotely disposed with respect to the plate, wherein the signal is directed from the at least one proximity-sensing device to the receiving unit by a transmission device selected from the group consisting of a cable and a wireless data transmission system.

10. A device according to claim 9 wherein the wireless data transmission system is selected from the group consisting of an ultrasonic wireless transmission system and a radio frequency transmission system.

11. A system adapted to dynamically measure a pressure exerted on a sample contained within a cylindrical mold of a gyratory, compactor said system comprising:
    an open-ended cylindrical mold having an inner diameter, the mold being adapted to contain a sample therein for compaction by the gyratory compactor;
    a rigid disk-shaped plate defining an axis and a periphery and having a diameter corresponding substantially to the inner diameter of the cylindrical mold, the plate being adapted to be disposed within the mold in communication with the sample; and
    at least one proximity-sensing device operably engaged with the plate, the at least one proximity-sensing device being configured to dynamically measure a proximity of a reference member with respect to the at least one proximity-sensing device and to produce therefrom a signal corresponding to the pressure exerted on the sample within the mold.

12. A system according to claim 11 wherein the plate further comprises a disk-shaped base portion having a center and opposing faces and a ring-shaped portion coaxial with the center and extending from the periphery of one of the faces, the center being configured to experience a deflection with respect to the periphery in response to pressure applied across the other face of the base portion.

13. A system according to claim 12 wherein the reference member is disposed on the base portion of the plate, away from the center and adjacent to the ring-shaped portion, and wherein the at least one proximity-sensing device is mounted on a distal end of an arm adjacent to the reference member, the arm having a proximal end mounted at the center and extending to the distal end substantially parallel to the base portion, the deflection of the center in response to pressure resulting in a corresponding displacement of the arm and the at least one proximity-sensing device parallel to the axis, the reference member being configured with respect to the at least one proximity-sensing device such that the displacement of the arm parallel to the axis and away from the reference member is sensed by the at least one proximity-sensing device, the corresponding signal produced by the at least one proximity-sensing device thereby being indicative of the pressure exerted on the sample within the mold.

14. A system according to claim 13 wherein the at least one proximity-sensing device further comprises at least one magnetic flux-sensitive transducer.

15. A system according to claim 14 wherein the reference member comprises a permanent magnet.

16. A system according to claim 11 wherein the at least one proximity-sensing device is selected from the group consisting of a Hall effect transducer, a magnetoresistor, a magnetic sensor, an accelerometer device, an electro-optical device, an inductive/capacitance device, a proximity sensor, and combinations thereof.

17. A system according to claim 11 further comprising a receiving unit configured to receive the signal from the at least one proximity-sensing device and to provide an indicia of the pressure exerted on the sample within the mold.

18. A system according to claim 11 further comprising a receiving unit operably engaged with the plate and configured to receive the signal from the at least one proximity-sensing device and to store the signal in a computer-readable manner.

19. A system according to claim 11 further comprising a receiving unit remotely disposed with respect to the plate, wherein the signal is directed from the at least one proximity-sensing device to the receiving unit by a transmission device selected from the group consisting of a cable and a wireless data transmission system.

20. A system according to claim 19 wherein the wireless data transmission system is selected from the group consisting of an ultrasonic wireless transmission system and a radio frequency transmission system.

21. A system adapted to dynamically measure a pressure exerted on a sample contained within a cylindrical mold of a gyratory compactor, said system comprising:
  a gyratory compactor apparatus;
  an open-ended cylindrical mold having a wall defining an inner diameter, the mold being configured to be operably engageable with the gyratory compactor apparatus and adapted to contain a sample therein for compaction by the gyratory compactor;
  a rigid disk-shaped plate defining an axis and a periphery and having a diameter corresponding substantially to the inner diameter of the mold, the plate being adapted to be disposed within the mold in communication with the sample; and
  at least one proximity-sensing device operably engaged with the plate, the at least one proximity-sensing device being configured to dynamically measure a proximity of a reference member with respect to the at least one proximity-sensing device and to produce therefrom a signal corresponding to the pressure exerted on the sample within the mold.

22. A system according to claim 21 wherein the plate further comprises a disk-shaped base portion having a center and opposing faces and a ring-shaped portion coaxial with the center and extending from the periphery of one of the faces, the center being configured to experience a deflection with respect to the periphery in response to pressure applied across the other face of the base portion.

23. A system according to claim 22 wherein the reference member is disposed on the base portion of the plate, away from the center and adjacent to the ring-shaped portion, and wherein the at least one proximity-sensing device is mounted on a distal end of an arm adjacent to the reference member, the arm having a proximal end mounted at the center and extending to the distal end substantially parallel to the base portion, the deflection of the center in response to pressure resulting in a corresponding displacement of the arm and the at least one proximity-sensing device parallel to the axis, the reference member being configured with respect to the at least one proximity-sensing device such that the displacement of the arm parallel to the axis and away from the reference member is sensed by the at least one proximity-sensing device, the corresponding signal produced by the at least one proximity-sensing device thereby being indicative of the pressure exerted on the sample within the mold.

24. A system according to claim 23 wherein the at least one proximity-sensing device further comprises at least one magnetic flux-sensitive transducer.

25. A system according to claim 24 wherein the reference member comprises a permanent magnet.

26. A system according to claim 21 wherein the at least one proximity-sensing device is selected from the group consisting of a Hall effect transducer, a magnetoresistor, a magnetic sensor, an accelerometer device, an electro-optical device, an inductive/capacitive device, a proximity sensor, and combinations thereof.

27. A system according to claim 21 further comprising a receiving unit configured to receive the signal from the at least one proximity-sensing device and to provide an indicia of the pressure exerted on the sample within the mold.

28. A system according to claim 21 further comprising a receiving unit operably engaged with the plate and configured to receive the signal from the at least one proximity-sensing device and to store the signal in a computer-readable manner.

29. A system according to claim 21 further comprising a receiving unit remotely disposed with respect to the plate, wherein the signal is directed from the at least one proximity-sensing device to the receiving unit by a transmission device selected from the group consisting of a cable and a wireless data transmission system.

30. A system according to claim 29 wherein the wireless data transmission system is selected from the group consisting of an ultrasonic wireless transmission system and a radio frequency transmission system.

31. A method of determining a pressure exerted on a sample contained within a cylindrical mold for a gyratory compactor said method comprising:
  inserting at least one proximity-sensing device into an open end of the mold, the mold having an inner diameter, the at least one proximity sensing device being operably engaged with a rigid disk-shaped plate defining an axis and a periphery and having a diameter corresponding substantially to the inner diameter of the mold, the plate further comprising a disk-shaped base portion having a center and opposing faces and a ring-shaped portion coaxial with the center and extending from the periphery of one of the faces, the center being configured to experience a deflection with respect to the periphery in response to pressure applied across the other face of the base portion, the at least one proximity-sensing device being mounted on a distal end of an arm having a proximal end mounted at the center and extending to the distal end substantially parallel to the base portion; and
  dynamically receiving a signal from the a least one proximity-sensing device as the mold is being gyrated by the gyratory compactor, the signal corresponding to a proximity of a reference member with respect to the at least one proximity-sensing device, the reference member being mounted on the base portion of the plate, away from the center and adjacent to the ring-shaped portion, so as to be adjacent to the at least one proximity-sensing device, the deflection of the center in response to pressure resulting in a corresponding displacement of the arm and the at least one proximity-sensing device parallel to the axis, the reference member being configured with respect to the at least one proximity-sensing device such that the displacement of the arm parallel to the axis and away from the reference member is sensed by the at least one proximity-sensing device, the corresponding signal produced by the at least one proximity-sensing device thereby being indicative of the pressure exerted on the sample within the mold.

32. A method according to claim 31 wherein inserting at least one proximity-sensing device further comprises inserting at least one proximity-sensing device, selected from the group consisting of a Hall effect transducer, a magnetoresistor, a magnetic sensor, an accelerometer device, an electro-optical device, an inductive/capacitive device, a proximity sensor, and combinations thereof, into an open end of the mold.

33. A method according to claim 31 wherein inserting at least one proximity-sensing device further comprises inserting at least one proximity-sensing device, comprising at least one magnetic flux-sensitive transducer, into an open end or the mold so as to be adjacent to the reference member, comprising a permanent magnet, the transducer being configured such that a magnetic flux through the transducer from the magnet varies as a function of the proximity of the reference member with respect to the at least one proximity-sensing device.

34. A method according to claim 31 wherein receiving a signal from the at least one proximity-sensing device further comprises receiving a signal from the at least one proximity-sensing device at a receiving unit configured provide an indicia of the pressure exerted on the sample within the mold.

35. A method according to claim 31 wherein receiving a signal from the at least one proximity-sensing device further comprises receiving a signal from the at least one proximity-sensing device at a receiving unit operably engaged with the plate, the receiving unit being configured to receive the signal and to store the signal in a computer-readable manner.

36. A method according to claim 31 wherein receiving a signal from the at least one proximity-sensing device further comprises receiving a signal from the at least one proximity-sensing device at a receiving unit remotely disposed with respect to the plate, the signal being directed from the at least one proximity-sensing device to the receiving unit by a transmission device selected from the group consisting of a cable and a wireless data transmission system.

37. A method according to claim 36 wherein receiving the signal at the receiving unit further comprises receiving the signal at the receiving unit by way of a transmission device operably engaged with the at least one proximity-sensing device and selected from the group consisting of a cable and a wireless data transmission system.

38. A method according to claim 37 wherein receiving the signal at the receiving unit by way or a wireless data transmission system further comprises receiving the signal at the receiving unit by way of a wireless data transmission system selected from the group consisting of an ultrasonic wireless transmission system and a radio frequency transmission system.

* * * * *

UNITED STATES PATENT AND TRADEMARK OFFICE
CERTIFICATE OF CORRECTION

PATENT NO. : 6,868,738 B2
DATED : March 22, 2005
INVENTOR(S) : William Matthew Moscrip and William A. Gowan It is certified that error appears in the above-identified patent and that said Letters Patent is hereby corrected as shown below:

Column 16,
Line 2, delete the "a" after "member";

Column 17,
Line 13, "capacitance" should read -- capacitive --;

Column 19,
Line 28, "end or" should read -- end of --;

Column 20,
Line 28, "way or" should read -- way of --.

Signed and Sealed this

Thirty-first Day of May, 2005

JON W. DUDAS
*Director of the United States Patent and Trademark Office*